US011185225B2

(12) United States Patent
Heeren et al.

(10) Patent No.: US 11,185,225 B2
(45) Date of Patent: *Nov. 30, 2021

(54) SURGICAL MICROSCOPE WITH INTEGRATED OPTICAL COHERENCE TOMOGRAPHY AND DISPLAY SYSTEMS

(71) Applicant: NOVARTIS AG, Basel (CH)

(72) Inventors: Tammo Heeren, Aliso Viejo, CA (US); Hugang Ren, Cypress, CA (US); Vadim Shofman, Irvine, CA (US); Lingfeng Yu, Rancho Santa Margarita, CA (US)

(73) Assignee: Alcon Inc., Fribourg (CH)

( * ) Notice: Subject to any disclaimer, the term of this patent is extended or adjusted under 35 U.S.C. 154(b) by 694 days.

This patent is subject to a terminal disclaimer.

(21) Appl. No.: 15/791,857

(22) Filed: Oct. 24, 2017

(65) Prior Publication Data

US 2018/0045927 A1 Feb. 15, 2018
US 2019/0212533 A9 Jul. 11, 2019

Related U.S. Application Data

(63) Continuation of application No. 14/827,473, filed on Aug. 17, 2015, now Pat. No. 9,826,900.

(51) Int. Cl.
*A61B 3/13* (2006.01)
*A61B 3/10* (2006.01)
(Continued)

(52) U.S. Cl.
CPC ............ *A61B 3/132* (2013.01); *A61B 3/0025* (2013.01); *A61B 3/102* (2013.01); *A61B 3/12* (2013.01);
(Continued)

(58) Field of Classification Search
CPC ....... A61B 3/132; A61B 3/0025; A61B 3/102; A61B 3/12; G02B 13/16; G02B 13/04; G02B 15/24
(Continued)

(56) References Cited

U.S. PATENT DOCUMENTS

| 2014/0024949 | A1* | 1/2014 | Wei ................... G02B 21/0012 600/476 |
| 2015/0077705 | A1* | 3/2015 | Artsyukhovich ...... A61B 3/102 351/206 |
| 2017/0164829 | A1* | 6/2017 | Awdeh .................. G02B 21/22 |

OTHER PUBLICATIONS

Richa et al. "Vision-Based Proximity Detection in Retinal Surgery" IEEE Transactions on Biomedical Engineering, vol. 59, No. 8, pp. 2291-2301 (Year: 2012).*

* cited by examiner

*Primary Examiner* — George G King

(57) ABSTRACT

An ophthalmic surgical microscope includes a beam coupler positioned along an optical path of the surgical microscope between a first eyepiece and magnifying/focusing optics, the beam coupler operable to direct the OCT imaging beam along a first portion of the optical path of the surgical microscope between the beam coupler and a patient's eye (an OCT image being generated based on a reflected portion of the OCT imaging beam). The surgical microscope additionally includes a real-time data projection unit operable to project the OCT image generated by the OCT system and a beam splitter positioned along the optical path of the surgical microscope between a second eyepiece and the magnifying/focusing optics. The beam splitter is operable to direct the projected OCT image along a second portion of the optical path of the surgical microscope between the beam splitter and the second eyepiece such that the projected OCT image is viewable through the second eyepiece.

1 Claim, 8 Drawing Sheets

(51) Int. Cl.
*A61B 3/00* (2006.01)
*A61B 3/12* (2006.01)
*G02B 13/04* (2006.01)
*G02B 13/16* (2006.01)
*G02B 15/24* (2006.01)

(52) U.S. Cl.
CPC .............. *G02B 13/04* (2013.01); *G02B 13/16* (2013.01); *G02B 15/24* (2013.01)

(58) Field of Classification Search
USPC ........................................................ 351/206
See application file for complete search history.

SURGICAL MICROSCOPE WITH INTEGRATED OPTICAL COHERENCE TOMOGRAPHY AND DISPLAY SYSTEMS

CROSS REFERENCE TO RELATED APPLICATIONS

The present application is a continuation of U.S. application Ser. No. 14/824,473, filed Aug. 17, 2015, titled "SURGICAL MICROSCOPE WITH INTEGRATED OPTICAL COHERENCE TOMOGRAPHY AND DISPLAY SYSTEMS," (now allowed), the disclosure of which is incorporated by reference in its entirety.

FIELD

The present disclosure relates generally to surgical microscopes for ophthalmic surgeries and, more particularly, to a surgical microscope with integrated optical coherence tomography (OCT) and display systems.

BACKGROUND

Ophthalmic surgeons often rely on surgical microscopes during ophthalmic surgical procedures to see fine details of a patient's eye. One class of ophthalmic surgeries, the vitreo-retinal procedure, involves vitrectomy, the removal of the vitreous body from the posterior chamber to access the retina. The successful execution of vitrectomy requires an essentially complete removal of the vitreous, including the most challenging regions near the vitreous base. Due to the transparent nature of the vitreous, performing a vitrectomy relying on only a conventional surgical microscope for visualization may be challenging.

To assist in visualization, surgeons may rely on pre-surgical optical coherence tomography (OCT) imaging. OCT imaging is a technique that enables visualization of the target tissue in depth by focusing a laser beam onto the target, collecting the reflected beam, interfering the reflected beam with a reference beam and detecting the interference, and measuring the reflectance signature within the depth of focus of the beam. The result is a line scan in depth, a cross-sectional scan, or a volumetric scan. During a surgical procedure, a surgeon may reference the previously-generated OCT scan to assist in visualization. However, systems providing real-time, intra-surgical OCT imaging to assist in visualization remain lacking.

SUMMARY

In certain embodiments, an ophthalmic surgical microscope includes a beam coupler positioned along an optical path of the ophthalmic surgical microscope between a first eyepiece and magnifying/focusing optics, the beam coupler operable to direct the OCT imaging beam along a first portion of the optical path of the surgical microscope between the beam coupler and a patient's eye (an OCT image being generated based on a portion of the OCT imaging beam reflected by a patient's eye). The ophthalmic surgical microscope additionally includes a real-time data projection unit operable to project the OCT image generated by the OCT system and a beam splitter positioned along the optical path of the ophthalmic surgical microscope between a second eyepiece and the magnifying/focusing optics. The beam splitter is operable to direct the projected OCT image along a second portion of the optical path of the surgical microscope between the beam splitter and the second eyepiece such that the projected OCT image is viewable through the second eyepiece.

Certain embodiments of the present disclosure may provide one or more technical advantages. For example, integrating the OCT system with the ophthalmic surgical microscope as described herein may allow the OCT scan range to be automatically adjusted as a surgeon manipulates the microscope field of view via the magnifying/focusing optics of the microscope, thus simplifying the surgery by reducing the number of adjustments the surgeon needs to make. Additionally, integrating the display system (referred to as a real-time data projection unit) in the manner described herein may allow a surgeon to view OCT images generated by the OCT system through the eyepiece(s) of the ophthalmic surgical microscope, thus eliminating the need for the surgeon to look away from the patient's eye to view a separate display monitor.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
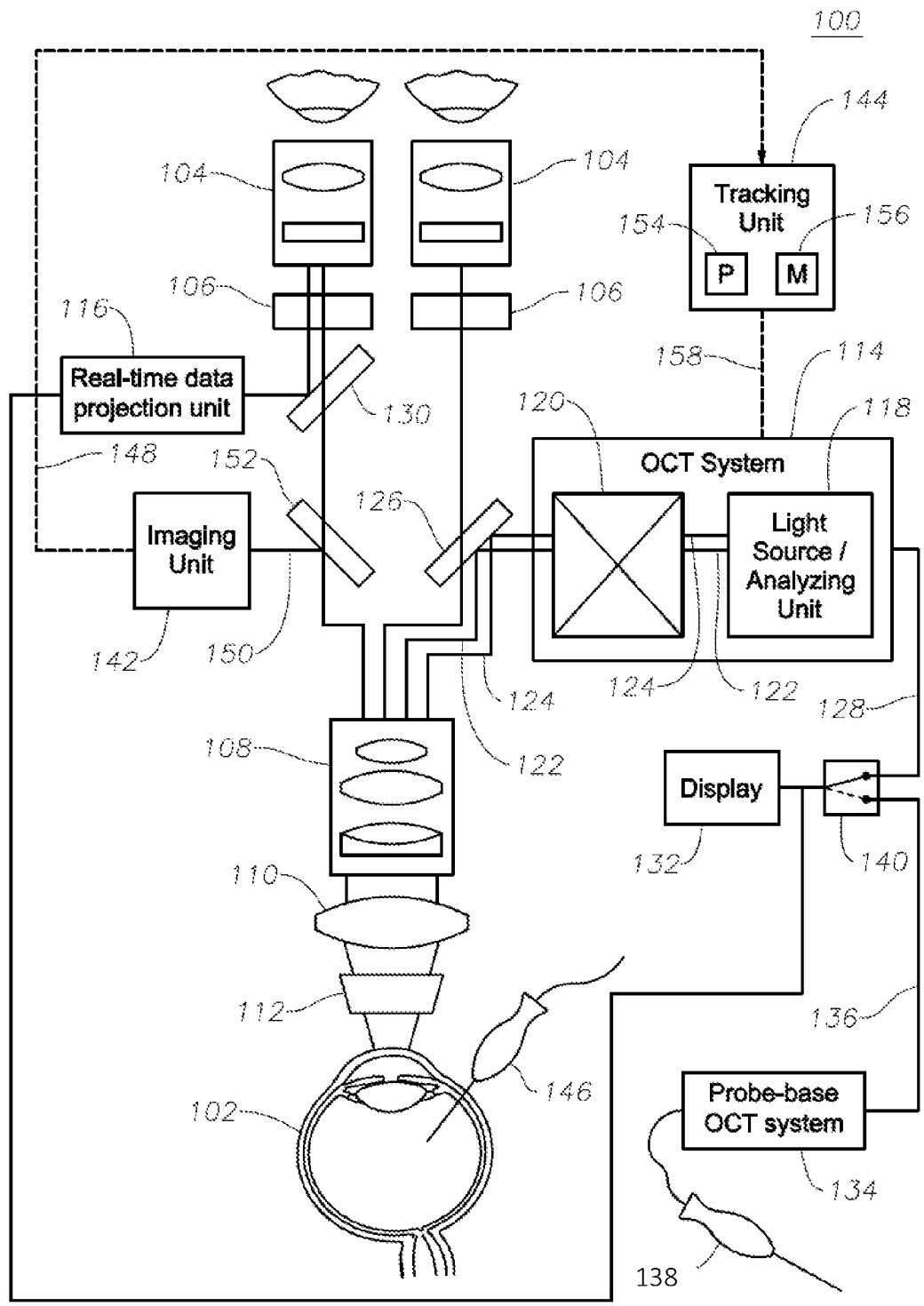
FIG. 1 illustrates an exemplary ophthalmic surgical microscope having integrated OCT and display systems, according to certain embodiments of the present disclosure.

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It should nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

In general, the present disclosure may provide a surgical microscope with integrated OCT and display systems. The integrated OCT system may be coupled to the optical path of the microscope optics at a point between the magnifying/focusing optics of the microscope and an eyepiece of the microscope. As a result, the OCT scan range may be automatically adjusted as a surgeon manipulates the microscope field of view via the magnifying/focusing optics of the microscope. The display system (referred to herein as a real-time data projection unit) may also be coupled to the optical path of the surgical microscope such that the OCT images generated by the OCT system may be viewed by a surgeon without the need to look at a separate display monitor.

FIG. 1 illustrates an exemplary ophthalmic surgical microscope 100 having integrated OCT and display systems, according to certain embodiments of the present disclosure. Ophthalmic surgical microscope 100 may facilitate magnified viewing of a patient's eye 102 during a surgical procedure and may generally include eyepieces 104, a relay lens 106, magnifying/focusing optics 108, an objective lens 110, and surgical viewing optics 112. Each of eyepieces 104, relay lens 106, magnifying/focusing optics 108, objective lens 110, and surgical viewing optics 112 may include any suitable optical components as understood by persons of ordinary skill in the art. Ophthalmic surgical microscope 100 may additionally include an integrated OCT system 114 operable to generate OCT images of the patient's eye 102 and a real-time data projection unit 116 operable to display those OCT images to a surgeon via one or both eyepieces 104. The location at which OCT system 114 is integrated into surgical microscope 100 (as discussed in further detail below) may advantageously allow the OCT scan range to be automatically adjusted as a surgeon manipulates the microscope field of view via the magnifying/focusing optics 108. Moreover, real-time data projection unit 116 may advantageously allow a surgeon to view the OCT images generated by OCT system 114 without the need to look at a separate display monitor.

OCT system 114 may include a light source/analyzing unit 118 and a beam scanner 120. In general, light source/analyzing unit 118 may generate an OCT imaging beam 122 and beam scanner 120 (in conjunction with other optical components of the surgical microscope) may direct the generated OCT imaging beam 122 to a particular region within the patient's eye 102. Reflections of the OCT imaging beam 122 from the particular region within the patient's eye 102 (reflected OCT imaging beam 124) may return to light source/analyzing unit 118 along the same optical path as OCT imaging beam 122, and light source/analyzing unit 118 may generate OCT images of the particular region by determining interference between the reflections 124 and a reference arm of the OCT imaging beam 122. The present disclosure contemplates that OCT system 114 may include any suitable additional optical components for manipulating OCT imaging beam 122 as would be understood by those of skill in the art, and those additional components are not depicted/described for the sake of simplicity.

In certain embodiments, the OCT imaging beam 122 may comprise an infrared or near infrared light beam covering a relatively narrow band of wavelengths (e.g., 830 nm-870 nm, 790 nm-900 nm, 950 nm-1150 nm). However, an OCT imaging beam 122 having any suitable spectral range may be used. The OCT imaging beam 122 may pass through beam scanner 120 (described in further detail below) along with any other suitable optical components of OCT system 114 (not depicted, as described above). OCT imaging beam 122 may then be directed to the patient's eye 102 via one or more of the above-described optical components of surgical microscope 100 (as described in further detail below).

Beam scanner 120 may comprise any suitable optical component or combination of optical components facilitating focusing of the OCT imaging beam 122 in the X-Y plane. For example, beam scanner 120 may include one or more of a pair of scanning mirrors, a micro-mirror device, a MEMS based device, a deformable platform, a galvanometer-based scanner, a polygon scanner, and/or a resonant PZT scanner. In certain embodiments, the position of the optical components of beam scanner 120 may be manipulated in an automated manner. As just one example, beam scanner 120 may comprise a pair of scanning mirrors each coupled to a motor drive, the motor drives operable to rotate the mirrors about perpendicular axes. As a result, by controlling the position of the coupled motors (e.g., according to a pre-determined or selected scan pattern), the X-Y positioning of OCT imaging beam 122 within the patient's eye 102 can be controlled. Additionally, the depth of focus of the OCT imaging beam 122 may be controlled by one or more other components of OCT system 114 as is understood in the art in order to facilitate 3-D OCT imaging.

As described above, reflected OCT beam 124 may return to OCT system 114 along substantially the same optical path as traveled by OCT imaging beam 122. Once reflected OCT beam 124 reaches light source/analyzing unit 118, light source/analyzing unit 118 may construct an OCT image (A-scan) based on interference between the reflected OCT beam 124 and a reference arm of OCT imaging beam 122 (as is known in the art). Moreover, by moving the imaging beam in the X-Y plane via beam scanner 120 and/or changing the depth of focus of the imaging beam 122, a plurality of OCT images (A-scans) may be generated and combined into an OCT cross sectional image (B-scan), and a plurality of those cross sectional images (B-scans) may be combined to generate a 3-D OCT image.

In certain embodiments, OCT system 114 may be integrated into surgical microscope 100 via a beam coupler 126 located in the optical path of the surgical microscope 100. Beam coupler 126 may include an optical element configured to reflect wavelengths in the spectral range of the OCT imaging beam 122 (e.g., infrared wavelengths) while allowing passage of light in the visible spectrum passing through surgical microscope 100. As one example, beam coupler 126 may comprise one of a dichroic hot mirror, a polarizing beamsplitter, and a notch filter.

In certain embodiments, beam coupler 126 may be located along the optical path between the surgical viewing optics 112 and an eyepiece 104. Surgical viewing optics 112 may include a drop-on macular lens, contact-based wide-angle lens, noncontact-based viewing system such as (binocular indirect ophthalmomicroscope) BIOM, or any other suitable viewing optics. More particularly, beam coupler 126 may be located along the optical path between magnifying/focusing optics 108 and an eyepiece 104. As a result, OCT imaging beam 122 will pass through magnifying/focusing optics 108, allowing the OCT scan range to be automatically adjusted as a surgeon manipulates the microscope field of view via the magnifying/focusing optics 108. The present disclosure contemplates that, although not depicted, OCT system 114 may additionally include any suitable optical components facilitating appropriate focus of OCT imaging beam 122 within the patient's eye 102 in light of the fact that the OCT imaging beam 116 passes through magnifying/focusing optics 108 and objective lens 110.

In certain embodiments, OCT system 114 may generate a visible aiming beam (not depicted) in addition to OCT imaging beam 122. This visible aiming beam may be visible to the surgeon via eyepieces 104 and may assist the surgeon in directing OCT imaging. In such embodiments, beam coupler 126 may be configured to reflect both the spectral range of the OCT imaging beam 122 (e.g., infrared wavelengths) and a narrow band of visible light (the aiming beam falling within that narrow band) while allowing passage of visible light passing through surgical microscope 100 that falls outside the narrow band of the aiming beam.

The OCT image(s) generated by OCT system 114 (identified in FIG. 1 by reference numeral 128), which may include an A-scan, a B-scan, or a 3-D OCT image constructed by combining a plurality of B-scans as described above, may be communicated to real-time data projection unit 116 for display to a surgeon via one or both eyepieces 104. Real-time data projection unit 116 may include any suitable device for projecting an image and may include any suitable optics (not depicted) for focusing that image. For example, real-time data projection unit 116 may comprise one of a heads-up-display, a one-dimensional display array, a two-dimensional display array, a screen, a projector device, or a holographic display.

In certain embodiments, real-time data projection unit 116 may be integrated into surgical microscope 100 via a beam splitter 130 located in the optical path of the surgical microscope 100. Beam splitter 130 may include an optical element configured to reflect the projected image generated by real-time data projection unit 116 toward eyepiece(s) 104 without substantially interfering with visible light reflected from the patient's eye 102.

In certain embodiments, surgical microscope 100 may additionally include a probe-based OCT system 134. Probe-based OCT system 134 may generate OCT images 136 is substantially the same manner as described above with regard to OCT system 114 except that the OCT imaging beam generated by probe-based OCT system 134 may be directed within the patient's eye 102 using a probe 138 inserted into the patient's eye 102. In embodiments including both an OCT system 114 and a probe-based OCT system 134, surgical microscope 100 may additionally include a source selection unit 140. Source selection unit 140 may include any suitable switch allowing selection either OCT images 128 (generated by OCT system 114) or OCT images 136 (generated by probe-based OCT system 134) for communication to real-time data projection unit 116 or display 132. As a result, a surgeon may select which OCT imaging system to use for imaging during surgery.

In certain embodiments, the OCT images projected by real-time data projection unit 116 (e.g., OCT images 128 and/or OCT images 136) may be displayed as a semitransparent overlay aligned with the visible structures viewed by the surgeon via eyepieces 104. In such embodiments, alignment between the OCT images and the actual structures of the eye may be achieved, for example, based on retinal tracking (described further below), instrument tracking (described further below), an aiming beam, or any combination thereof.

In certain other embodiments, the OCT images projected by real-time data projection unit 116 may be displayed in a corner of the field of view of the surgeon or any other suitable location in which they do not substantially impair the surgeon's ability to view the eye 102 through eyepieces 104.

Although real-time data projection unit 116 is described above as projecting OCT images 128 and/or OCT images 136 into the optical path of the surgical microscope 100 such that they are viewable through eyepiece(s) 104, the present disclosure contemplates that real-time data projection unit 116 may, additionally or alternatively, project any other suitable information (e.g., extracted and/or highlighted information from OCT data, fundus images, surgical parameters, surgical patterns, surgical indicators, etc.) into the optical path of the surgical microscope 100, according to particular needs.

In certain embodiments, surgical microscope 100 may additionally include an imaging unit 142 and a tracking unit 144. As described in further detail below, imaging unit 142 and tracking unit 144 may collectively facilitate OCT imaging that tracks the location of a surgical instrument 146 within the patient's eye 102. Additionally or alternatively, imaging unit 142 and tracking unit 144 may collectively facilitate OCT imaging that tracks the retina of the patient's eye 102.

Imaging unit 142 may include any suitable device for generating a fundus image 148 of a patient's eye 102 and may include suitable magnification and focusing optics (not depicted) for performing that function. As a simplified example, visible or near infrared light 150 reflected by the patient's eye 102 along the optical path of surgical microscope 100 may be directed toward imaging unit 142 via a mirror 152 placed along the optical path and operable to partially reflect such light. In certain embodiment, fundus images 148 may be discrete still photographs of the patient's eye 102. In other embodiment, the fundus image 148 may comprise a continuous video stream of the patient's eye 102. Example imaging units may include digital video cameras, line scan ophthalmoscopes or confocal-scanning ophthalmoscopes.

In the depicted embodiment, because the visible or near infrared light 150 is sampled from the optical path before OCT images are introduced into the optical path via real-time data projection unit 116, the generated fundus images 148 will not include the projected OCT images (which may be beneficial for the instrument tracking described below). Although imaging unit 142 is depicted and described as being located at particular position relative to the optical components of the surgical microscope 100 and OCT system 114, the present disclosure contemplates that imaging unit 142 may be placed at any suitable location relative to those components, according to particular needs.

Tracking unit 144 of surgical microscope 100 may be generally operable to determine the location and motion of surgical instrument 146 within the patient's eye 102 based at least in part on fundus images 148 generated by imaging unit 142. Tracking unit 144 may include any suitable combination of hardware, firmware, and software. In certain embodiments, tracking unit 144 may include a processing module 154 and a memory module 156. Processing module 154 may include one or more microprocessors, field-programmable gate arrays (FPGAs), controllers, or any other suitable computing devices or resources. Processing module 154 may work, either alone or with other components depicted in FIG. 1, to provide the functionality described herein. Memory module 156 may take the form of volatile or non-volatile memory including, without limitation, magnetic media, optical media, random access memory (RAM), read-only memory (ROM), removable media, or any other suitable memory component.

Tracking unit 144 may be programmed to (or may store software in memory module 156 that, when executed by processing module 154, is operable to) process the fundus images 148 generated by imaging unit 142 to determine and track the location of surgical instrument 146 within the patient's eye 102. For example, the processing module 154 may receive and process the images acquired by the imaging unit 142. The memory module 156 of the tracking unit 144 may store the pre-processed and/or post-processed image data. The processing module 154 may detect and calculate the location and/or orientation (or the change of the location and orientation) of the surgical instrument 146 in the surgical field based on the fundus images 148. Although tracking unit 144 is primarily described as tracking the location of a surgical instrument 146 within a patient's eye, the present disclosure contemplates that, additionally or alternatively, tracking unit 144 may track the location and/or motion of the patient's eye itself.

Tracking unit 144 may be communicatively coupled (via wired or wireless communication) to OCT system 114, and tracking unit 144 may be programmed to (or may store software in memory module 156 that, when executed by processing module 154, is operable to) generate signals 158 to be communicated to OCT system 114 to cause beam scanner 120 of OCT system 114 to direct the location of the OCT imaging beam 122 within the patient's eye 102.

For example, the signals 158 may be generated based on the determined location of the surgical instrument 146 within the patient's eye 102, and beam scanner 120 of OCT system 114 may direct OCT imaging beam 122 to a location in the vicinity of the tip of the surgical instrument 146. As a result, the OCT images 128 may be generated in an area of most interest to the surgeon. Moreover, in embodiments in which the OCT images 128 are displayed as a semi-transparent overlay in the field of view of the microscope, the tracking of the surgical instrument 146 may additionally facilitate proper positioning of that overlay.

As another example, the signals 158 may be generated based on a determined location of the retina of the patient's eye 102 (determined by tracking unit 144 by processing fundus images 148 in a manner similar to that discussed above with regard to tracking surgical instrument 146), and beam scanner 120 of OCT system 114 may direct OCT imaging beam 122 to constant location relative to the retina. Moreover, in embodiments in which the OCT images 128 are displayed as a semi-transparent overlay in the field of view of the microscope, the tracking of the retina may additionally facilitate proper positioning of that overlay.

Although surgical microscope 100 is depicted and described as including OCT images displayed through a fixed, single channel (i.e., real-time data projection unit 116 is coupled to the optical path of one of the two eyepieces 104), other embodiments are contemplated by the present disclosure (as described with regard to FIGS. 2A-2B, 3-4, and 5A-5C, below).

Figure 2A:
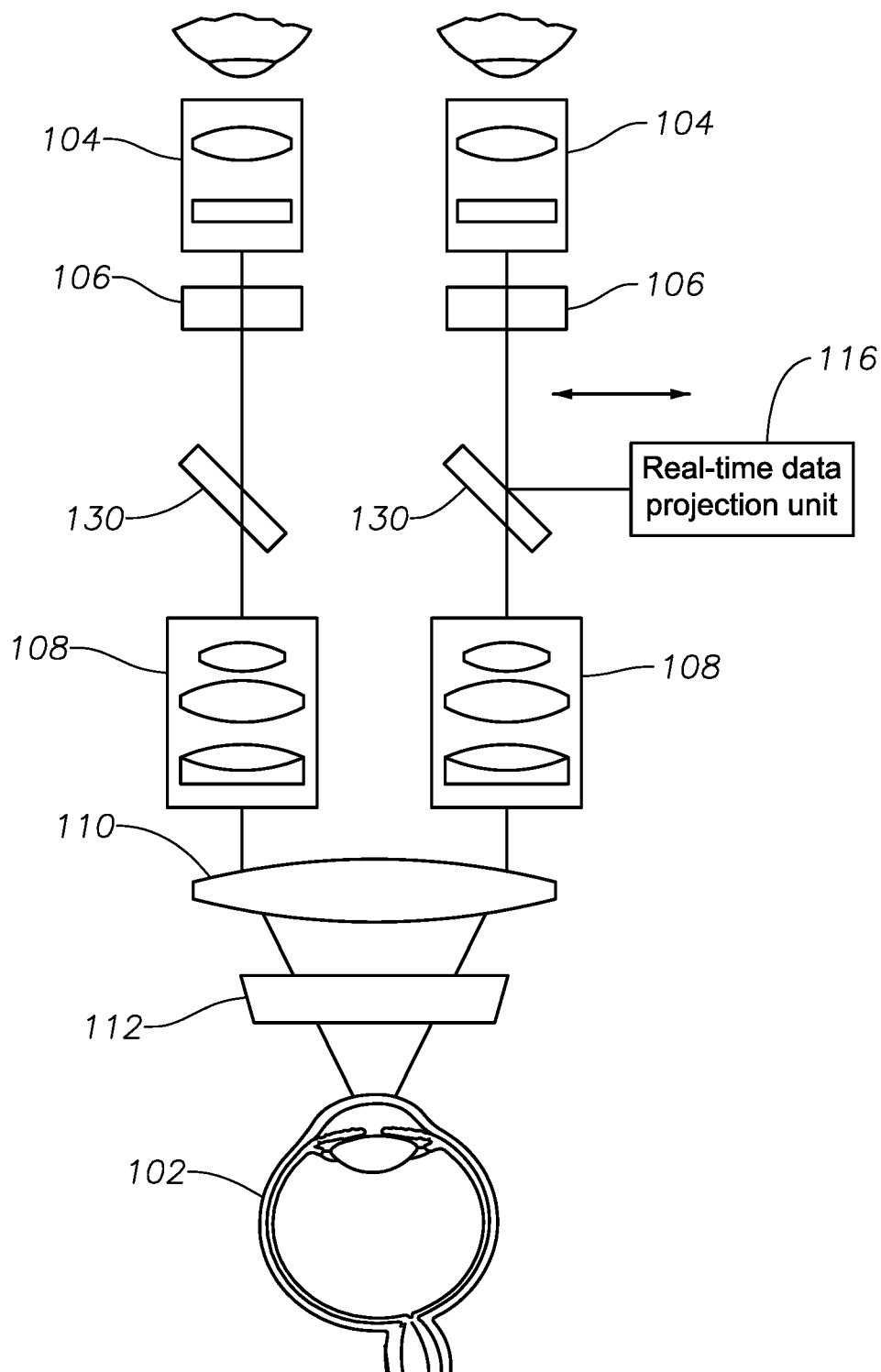
FIGS. 2A-2B illustrate embodiments of the ophthalmic surgical microscope depicted in FIG. 1 having switchable single channel data injection, according to certain embodiments of the present disclosure.
Figure 2B:
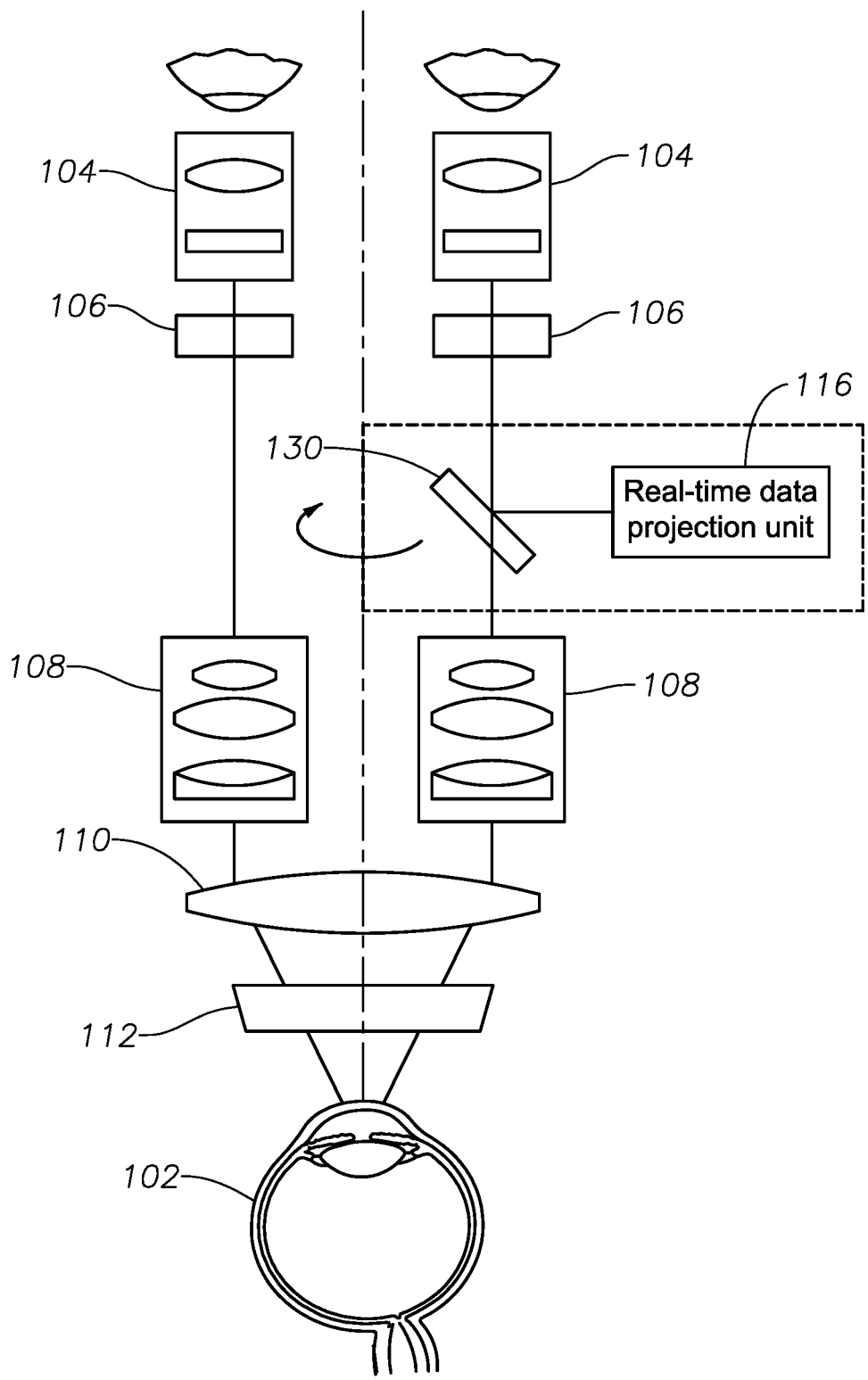

FIGS. 2A-2B illustrate embodiments of ophthalmic surgical microscope 100 having switchable single channel data injection, according to certain embodiments of the present disclosure. Although FIGS. 2A-2B do not depict certain components of ophthalmic surgical microscope 100 as depicted in FIG. 1 for the sake of simplicity, the present disclosure contemplates that those components be included and that they function in substantially the same manner as described above with regard to FIG. 1.

In the embodiment depicted in FIGS. 2A-2B, ophthalmic surgical microscope 100 includes a real-time data projection unit 116 capable of single channel data injection (i.e., the images injected by real-time data projection unit 116 are viewable through only one of the two eyepieces 104, as in FIG. 1). However, unlike the embodiment depicted in FIG. 1, the embodiment depicted in FIGS. 2A-2B provides the ability to change which channel (i.e., eyepiece 104) onto which the data is injected. More particularly, FIG. 2A depicts an embodiment in which one or both of real-time data projection unit 116 and beam splitter 130 can translate side to side in order to change the channel onto which data is injected while FIG. 2B depicts an embodiment in which the assembly of real-time data projection unit 116 and beam splitter 130 rotatable about a midpoint of surgical microscope 100 in order to change the channel onto which data is injected. As a result, a surgeon may be provided the flexibility to select which eye is used to view the injected data.

Figure 3:
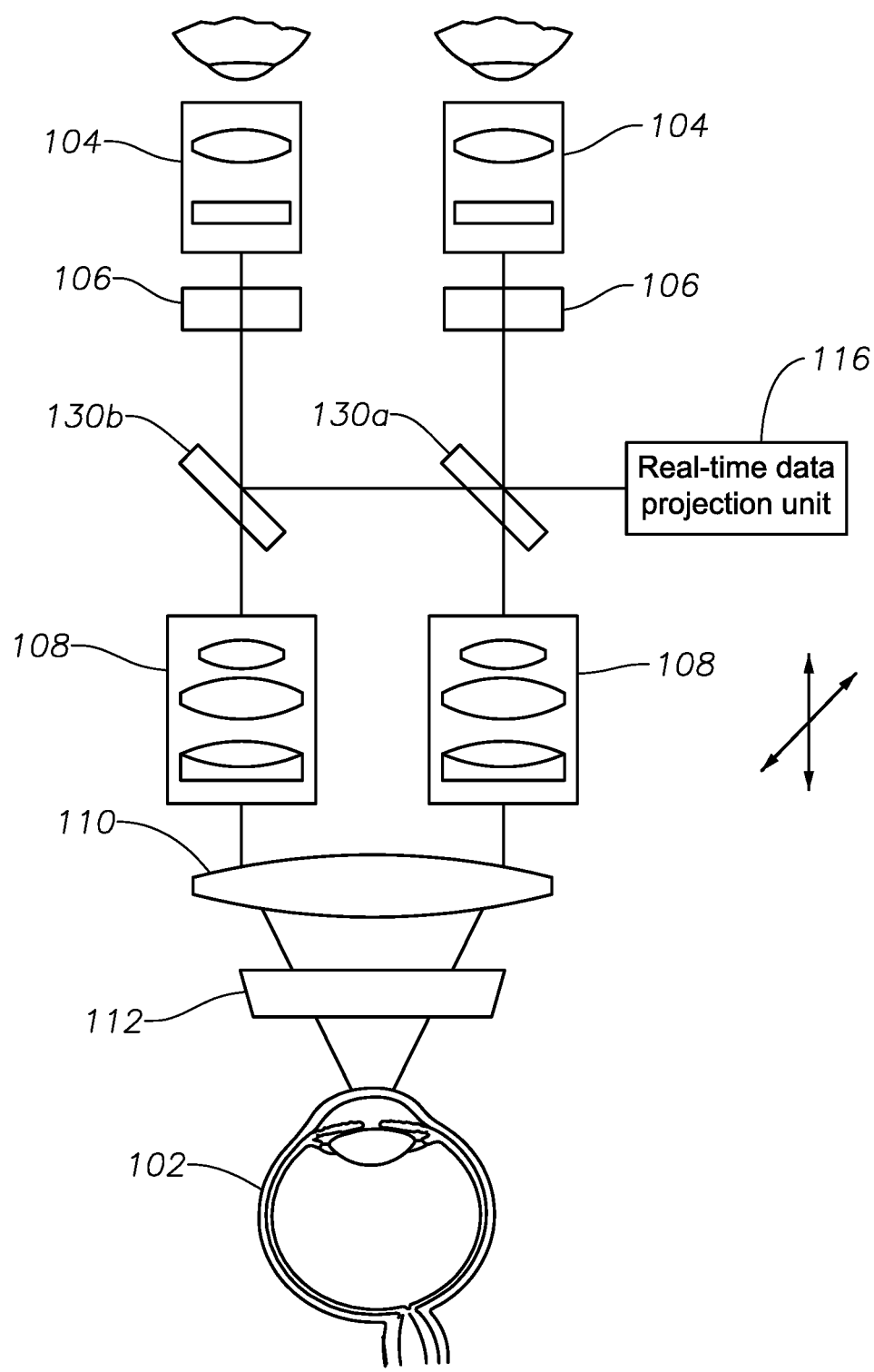
FIG. 3 illustrates an embodiment of the ophthalmic surgical microscope depicted in FIG. 1 having two-channel data injection, according to certain embodiments of the present disclosure.

FIG. 3 illustrates an embodiment of ophthalmic surgical microscope 100 having two-channel data injection, according to certain embodiments of the present disclosure. Although FIG. 3 does not depict certain components of ophthalmic surgical microscope 100 as depicted in FIG. 1 for the sake of simplicity, the present disclosure contemplates that those components be included and that they function in substantially the same manner as described above with regard to FIG. 1.

In the embodiment depicted in FIG. 3, surgical microscope 100 include a single real-time data projection unit 116 and two beam splitters 130 (130a and 130b) each associated with a corresponding channel of the microscope. Beam splitters 130a and 130b may be configured such that the data projected by real-time data projection unit 116 is duplicated and viewable via both of the eyepieces 104. Reflectivities of the beam splitters 130a and 130b may be selected such that the brightness of the image viewable through each eyepiece 104 is the same. Moreover, beam splitters may be movable in order to change the shifted within the surgeon's field of view. Alternatively, movement within the surgeon's field of view may be achieved by placing a beam deflection device (e.g., an acoustical optical deflector) in the optical path of the image projected by real-time data projection unit 116.

Figure 4:
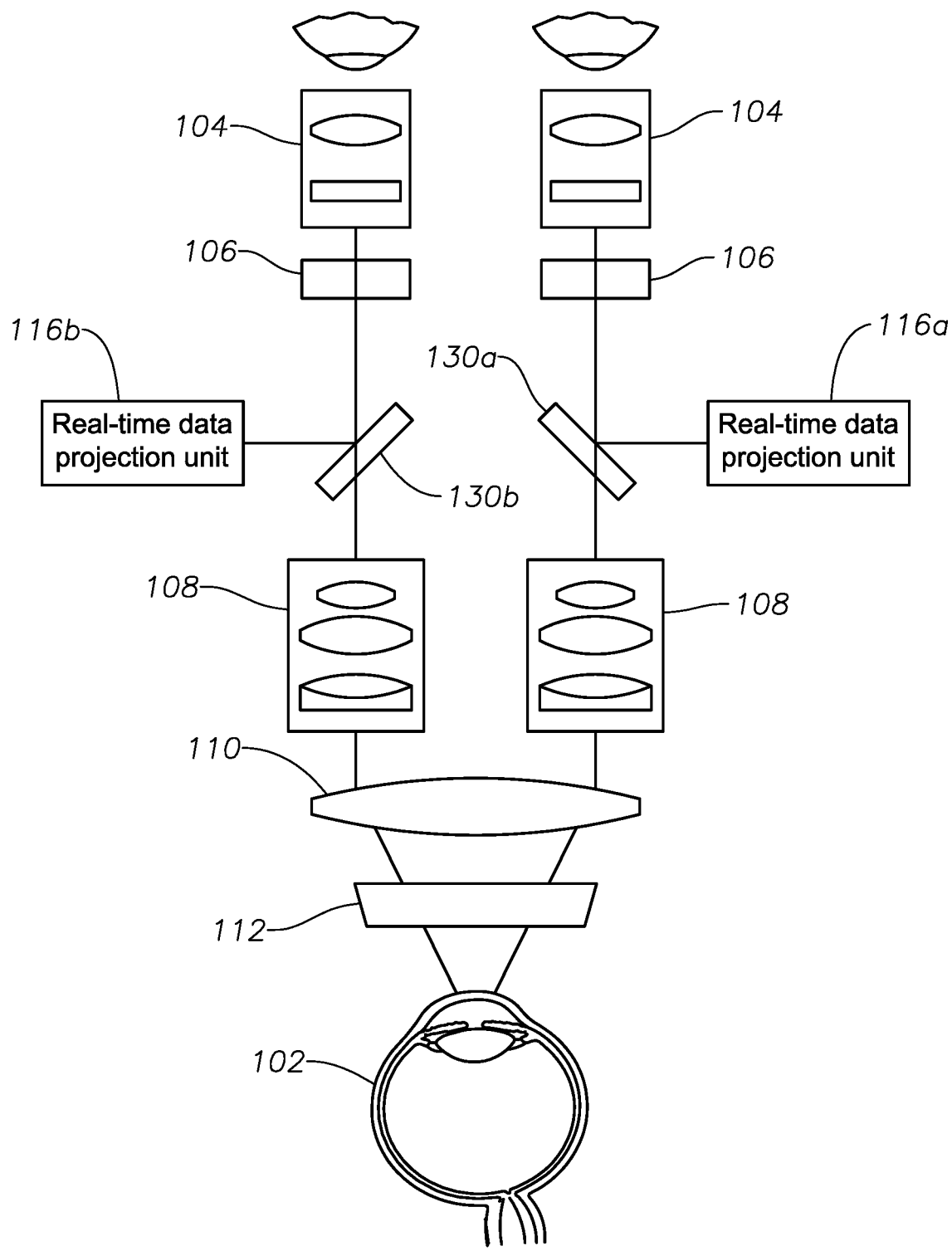
FIG. 4 illustrates an alternative embodiment of the ophthalmic surgical microscope depicted in FIG. 1 having two-channel data injection, according to certain embodiments of the present disclosure.

FIG. 4 illustrates an alternative embodiment of ophthalmic surgical microscope 100 having two-channel data injection, according to certain embodiments of the present disclosure. Although FIG. 4 does not depict certain components of ophthalmic surgical microscope 100 as depicted in FIG. 1 for the sake of simplicity, the present disclosure contemplates that those components be included and that they function in substantially the same manner as described above with regard to FIG. 1.

In the embodiment depicted in FIG. 4, two real-time data projection units 116 are includes (116a and 116b). Each real-time data projection unit projects an image, which is coupled into the optical path of the surgical microscope by a corresponding beam splitter 130. Because each real-time data projection unit can inject a unique image, the embodiment of FIG. 4 may facilitate 3-D perception. More particularly, each real-time data projection unit 116 may project the same image but with slightly different perspectives so as to provide 3-D perception when viewed through eyepieces 104.

Figure 5A:
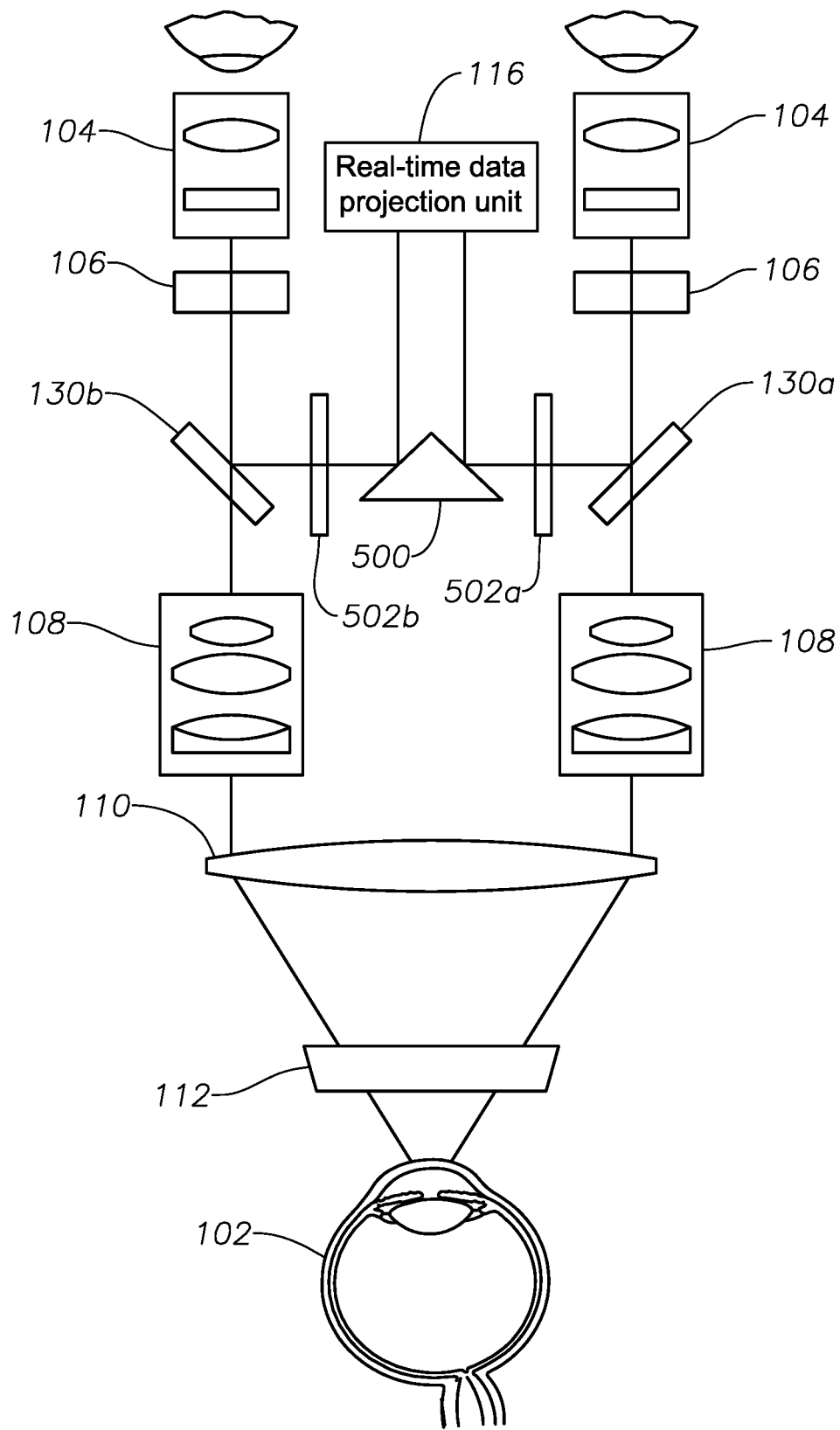
FIGS. 5A-5C illustrate embodiments of the ophthalmic surgical microscope depicted in FIG. 1 having two-channel data injection with 3-D perception, according to certain embodiments of the present disclosure.
Figure 5B:
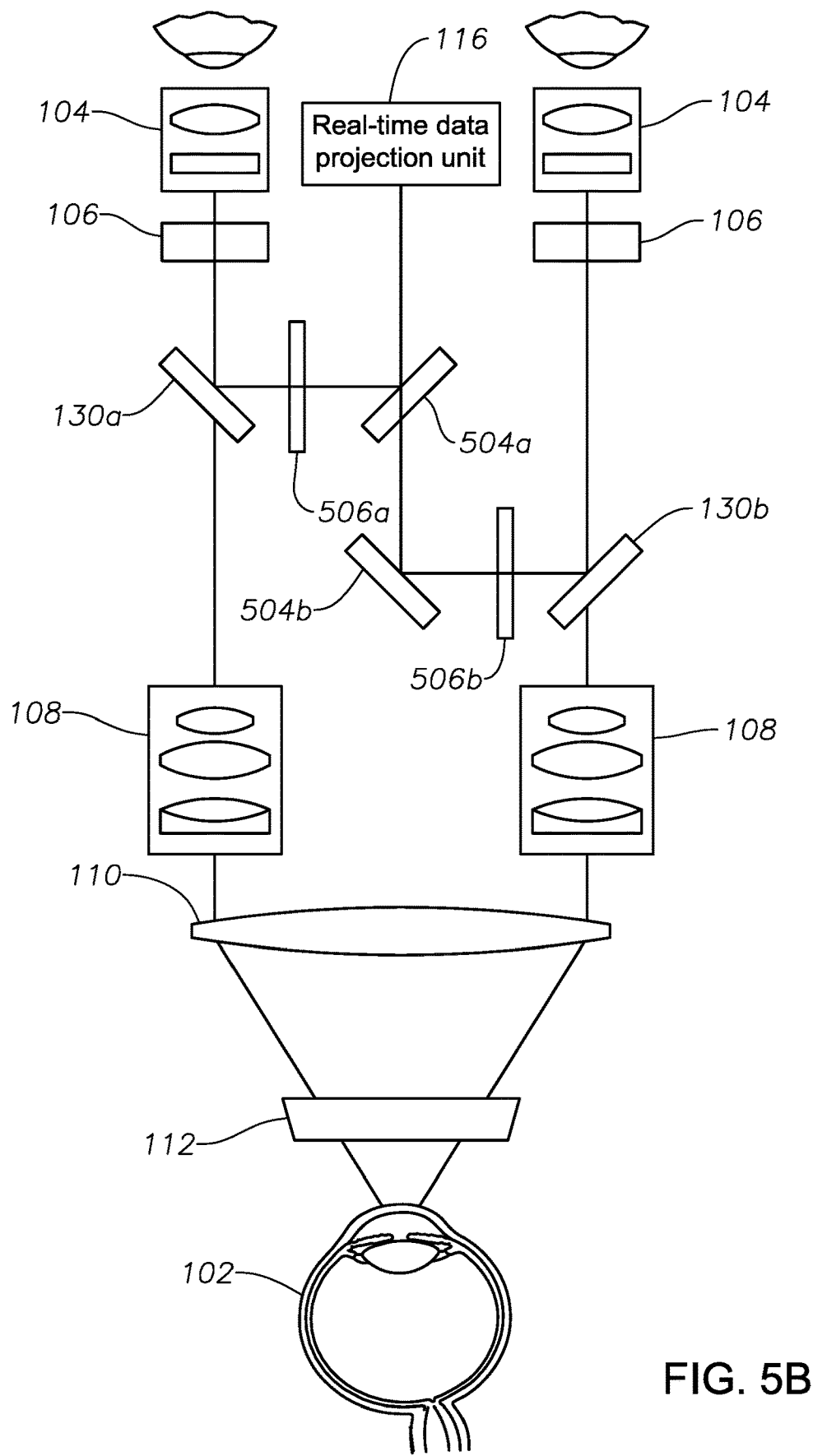
Figure 5C:
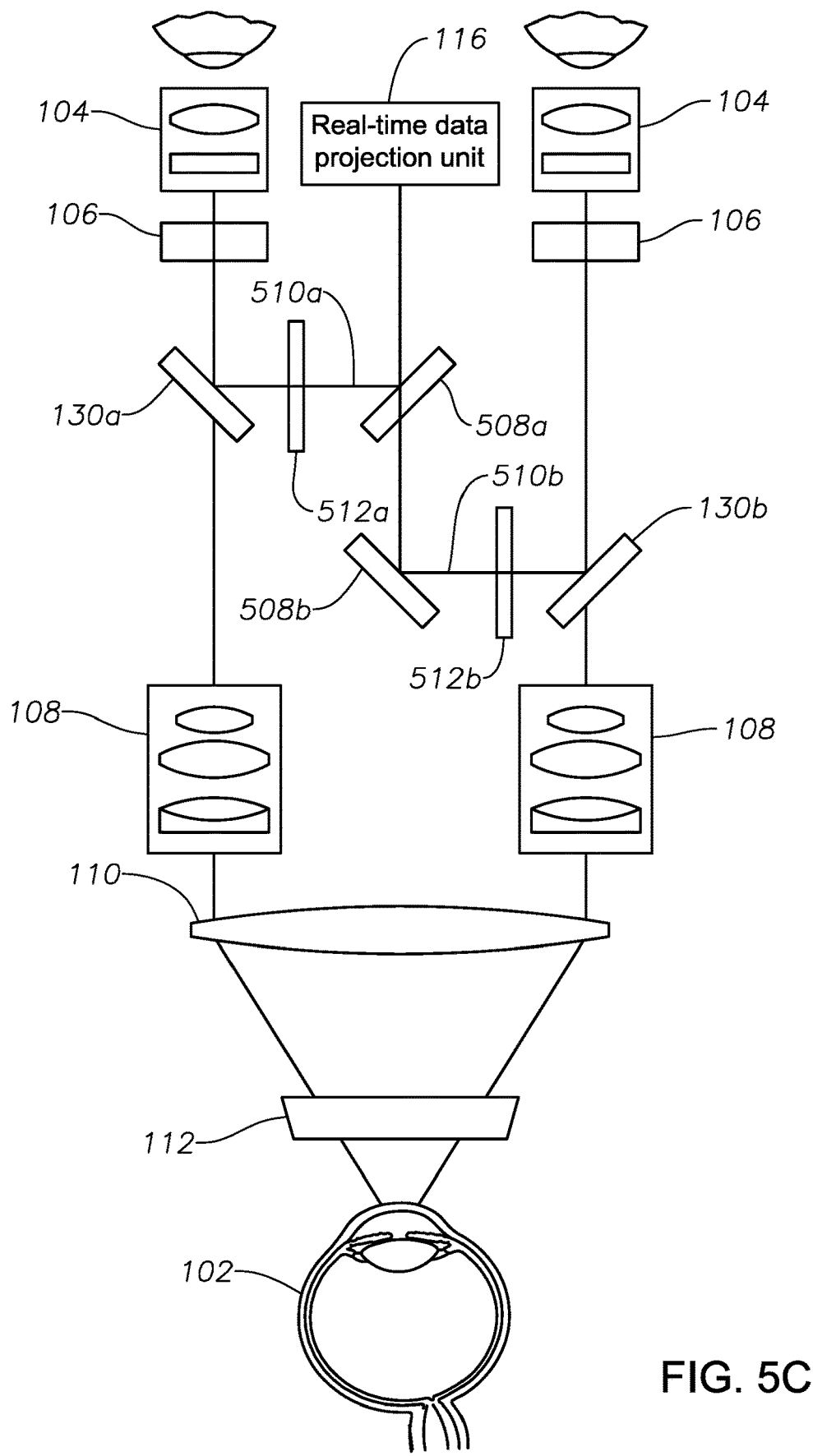

FIGS. 5A-5C illustrate embodiments of ophthalmic surgical microscope 100 having two-channel data injection with 3-D perception, according to certain embodiments of the present disclosure. Although FIGS. 5A-5C do not depict certain components of ophthalmic surgical microscope 100 as depicted in FIG. 1 for the sake of simplicity, the present disclosure contemplates that those components be included and that they function in substantially the same manner as described above with regard to FIG. 1.

In the embodiments depicted in FIGS. 5A-5C, 3-D perception is facilitated using one real-time data projection unit 116 rather than two (as in the embodiment described above with regard to FIG. 4). In the embodiment depicted in FIG. 5A, a single real-time data projection unit 116 projects side-by-side images, which may be slightly different to provide 3-D perception (as described above). The projected side-by-side images may be split by a beam splitter 500 and projected into each eyepiece 104 by beam splitter 130a and 130b. In certain embodiments, filters 502a and 502b may also be placed in the optical path of the projected images to further facilitate 3-D perception.

In the embodiment depicted in FIG. 5B, real-time data projection unit 116 may project a color-coded image (such as a red and cyan coded image in anaglyph), and that color coded image may pass through beam splitters 504a and 504b to be directed toward the two channels of surgical microscope 100. Filters 506a and 506b may be placed in the optical path of the image for each channel to separate the color-coded information. For example, filter 506a (such as a red filter) may be inserted into the left channel and filter 506b (such as a cyan filter) may be added to the right channel to separate the red/cyan information in the projected image. By properly calibrating the projected image, 3-D perception may be provided without the need for the surgeon to wear extra glasses or optical devices.

In the embodiment depicted in FIG. 5C, real-time data display unit 116 may be a polarized display/projector (such as a polarization modulated projector) and may project a polarization encoded image. The projected polarization encoded image may pass through polarizing beam splitters 508a and 508b to be divided between the two channels. For example, a p polarized image may be split into one eye (designated as 510a) while an s polarized image will be split into the other eye (designated as 510b). Additionally or alternatively, by inserting wave plates 512a and 512b into the two channels, a left hand circular polarized image may be split into one eye while a right hand circular polarized image may be split into the other eye. By properly calibrating the projected image, 3-D perception may be provided without the need for the surgeon to wear extra glasses or optical devices.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An ophthalmic surgical microscope, comprising:
an optical coherence tomography (OCT) system comprising an OCT light source for generating an OCT imaging beam;
a beam coupler for directing the OCT imaging beam along an optical path to a patient's eye, wherein at least a portion of the OCT imaging beam reflected by the patient's eye is returned to the OCT system, and wherein the OCT system generates an OCT image based on the reflected portion of the OCT imaging beam;
a real-time data projection unit for encoding the OCT image as a polarization-encoded OCT image and projecting the polarization-encoded OCT image;
a first beamsplitter for directing the OCT image projected by the real-time data projection to a first eyepiece of the ophthalmic surgical microscope such that the OCT image projected by the real-time data projection unit is viewable through the first eyepiece;
a second beamsplitter directs the OCT image projected by the real-time data projection unit to a second eyepiece of the ophthalmic microscope;
a first polarization beamsplitter configured to split the polarization-encoded OCT image into a first polarization-encoded OCT image and a second polarization-encoded OCT image and to direct the first polarization-encoded OCT image toward the first beamsplitter,
a reflector to direct the second polarization-encoded OCT image toward a second beamsplitter;
a first wave plate positioned between the first polarization beamsplitter and the first beamsplitter, wherein the first wave plate creates a left hand circular polarized image from the first polarization-encoded OCT image; and
a second wave plate positioned between the second polarization beamsplitter and the second beamsplitter, wherein the second wave plate creates a right hand circular polarized image from the second polarization-encoded OCT image;
wherein the first beamsplitter directs the left hand circular polarized image along a portion of the optical path of the ophthalmic surgical microscope such that the left hand circular polarized image is viewable through the first eyepiece,
wherein the second beamsplitter directs the right hand circular polarized image along a second portion of the optical path of the ophthalmic surgical microscope such that the right hand circular polarized image is viewable through the second eyepiece, and
wherein the right hand circular polarized image and the left hand circular polarized image generates 3-D perception of the OCT image in the first and second eyepiece.

* * * * *